(12) United States Patent
Kryzanski

(10) Patent No.: US 10,912,937 B2
(45) Date of Patent: Feb. 9, 2021

(54) METHODS AND DEVICES FOR GUIDED SUBDURAL ELECTRODE ARRAY PLACEMENT

(71) Applicant: Tufts Medical Center, Inc., Boston, MA (US)

(72) Inventor: James Kryzanski, Boston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 308 days.

(21) Appl. No.: 15/948,625

(22) Filed: Apr. 9, 2018

(65) Prior Publication Data
US 2019/0308008 A1 Oct. 10, 2019

(51) Int. Cl.
*A61B 5/05* (2021.01)
*A61B 5/0478* (2006.01)
*A61B 5/04* (2006.01)
*A61N 1/05* (2006.01)
*A61B 5/00* (2006.01)
*A61N 1/36* (2006.01)

(52) U.S. Cl.
CPC ........ *A61N 1/0531* (2013.01); *A61B 5/04001* (2013.01); *A61B 5/4064* (2013.01); *A61B 5/4094* (2013.01); *A61B 5/6868* (2013.01); *A61N 1/0529* (2013.01); *A61N 1/36064* (2013.01)

(58) Field of Classification Search
CPC ................................. A61N 1/05; A61N 1/0529
USPC ......................................................... 607/116
See application file for complete search history.

(56) References Cited

U.S. PATENT DOCUMENTS

| | | | |
|---|---|---|---|
| 6,024,702 A * | 2/2000 | Iversen | A61B 5/0422 600/378 |
| 8,364,237 B2 | 1/2013 | Stone et al. | |
| 9,820,668 B2 | 11/2017 | Hua | |
| 2003/0009207 A1* | 1/2003 | Paspa | A61N 1/0529 607/116 |
| 2004/0122360 A1* | 6/2004 | Waldhauser | A61M 25/0012 604/95.04 |

(Continued)

FOREIGN PATENT DOCUMENTS

WO WO-2011084788 A2 * 7/2011 ........... A61B 5/0482

OTHER PUBLICATIONS

Dixi Medical, "Microdeep depth electrode." Retrieved from http://www.diximedical.com/en/microdeep-depth-electrode on Apr. 9, 2018, 10 pages.

(Continued)

*Primary Examiner* — Jon Eric C Morales
(74) *Attorney, Agent, or Firm* — Occhiuti & Rohlicek LLP

(57) ABSTRACT

Disclosed are devices, electrodes, systems, methods, and other implementations, including a device that includes an electrode comprising an elongated body, a plurality of electrode contacts disposed on a first side of the elongated body, and a cannulation channel defined along a longitudinal axis of the electrode. The device further includes a guiding mechanism received within the cannulation channel, the guiding mechanism configured to guide the electrode for placement at a target area inside a body of a patient. In some embodiments, the cannulation channel is configured to receive irrigation fluids dispensed through a perforated end located near a leading tip of the elongated body.

32 Claims, 10 Drawing Sheets

(56) References Cited

U.S. PATENT DOCUMENTS

2005/0234507 A1* 10/2005 Geske ............... A61B 17/29
606/207
2010/0241100 A1 9/2010 Blumenfeld et al.
2016/0256062 A1 9/2016 Greger et al.
2017/0173340 A1* 6/2017 Gupte ............... A61N 1/0556

OTHER PUBLICATIONS

Greger, et al., "A chronically implantable, hybrid cannula-electrode device for assessing the effects of molecules on electrophysiological signals in freely behaving animals." J. Neurosci Methods. Jul. 30, 2007, 163(2): 321-325.

Du Hoffmann et al., "An inexpensive drivable cannulated microelectrode array for simultaneous unit recording and drug infusion in the same brain nucleus of behaving rats," J. Neurophysiol., Aug. 2011; 106(2): pp. 1054-1064.

Kaiboriboon et al., "Epilepsy surgery in the United States: Analysis of data from the National Association of Epilepsy Centers." Epilepsy Research 116 (2015) pp. 105-109.

Rolston et al., "Rate and Complications of Adult Epilepsy Surgery in North America: Analysis of Multiple Databases." Accepted Manuscript to Appeal in Epilepsy Research, Accepted date: May 5, 2016, 31 pages. http://dx.doi.org/10.1016/j.eplepsyres.2016.05.001.

* cited by examiner

METHODS AND DEVICES FOR GUIDED SUBDURAL ELECTRODE ARRAY PLACEMENT

BACKGROUND

Epilepsy will affect 1 in 26 Americans over their lifetimes and in 30% of cases medications are not effective in controlling the seizures. In these 'medically refractory' cases, surgical options should be considered given the malignant nature of uncontrolled seizures. Recent studies have concluded that epilepsy surgery is underutilized. Nevertheless, surgical procedures for intracranial electrode placement are common and increasing. Furthermore, recent technological advances such as responsive neurostimulation with the Neuropace™ system provide potential surgical options for patients who have seizures coming from multiple or eloquent brain areas and were previously not candidates. These patients nearly always require initial subdural electrode monitoring. Subdural electrodes are also used in cyberprosthetic devices where surface electrode recordings are used to move paralyzed limbs in patients with neurologic injury. Additional applications where electrodes may be used include responsive neurostimulation to treat epilepsy and cortical stimulation for chronic pain. These applications often rely on conventional subdural grid technology.

The crucial aspect of surgical evaluation is identifying the area(s) of the brain responsible for seizures and often this is done by intracranial electrode placement. Subdural, or brain surface, electrodes are often used in patients with refractory epilepsy to determine the seizure focus. The subdural space is the area between the brain surface and the dura, or fibrous covering, of the brain. The 'ictal zone', or area of seizure onset, is determined by the electrodes covering the area. Therefore, surgeons try to cover a large area of the cortex with electrodes in order to maximize the chance of finding the ictal zone. The current technique for placing a subdural electrode array involves surgery to remove a significant piece of the skull and then lay a subdural grid and numerous strip electrodes on the brain surface. The invasiveness and risk of this procedure is considerable.

Another technique that is used for the placement of brain electrodes is based on using stereo-EEG, where electrodes are placed into the brain itself and not on the brain surface through small skull drill holes in computer-determined trajectories. Though superficially less invasive than subdural electrode arrays, this technique requires multiple penetrations of the brain and does not optimally record from the brain surface, where most seizures arise. Placement of subdural electrodes through small drill holes is currently challenging because it is difficult to advance the electrode into the subdural space due to the initial sharp angle maneuvering (often close to 90°) necessary to advance the electrode under the skull and onto the brain surface. With this constraint it is challenging to apply a force vector that is tangential to the brain surface, and consequently the placement of subdural electrodes through a small drill hole risks brain injury due to inadvertent penetration. In addition, the broad, flat design of existing electrodes leads to crowding of components in the drill hole, making placement of even a small number of strips difficult if not impossible. This results in relatively poor surface coverage. Therefore it is not currently possible to place a large subdural electrode array through a small skull drill hole.

SUMMARY

Disclosed are devices, systems, methods, and other implementations to place electrode arrays (e.g., of subdural electrodes) through a small drill hole in the skull using a guiding mechanism, such as molded and flexible catheters, to navigate the electrodes into position.

In some variations, a device is provided that includes an electrode comprising an elongated body, a plurality of electrode contacts disposed on a first side of the elongated body, and a cannulation channel defined along a longitudinal axis of the electrode. The device further includes a guiding mechanism received within the cannulation channel, the guiding mechanism configured to guide the electrode for placement at a target area inside a body of a patient.

Embodiments of the device may include at least some of the features described in the present disclosure, including one or more of the following features.

The cannulation channel may be defined within the elongated body.

The device may further include a sleeve disposed on a second side of the elongated body of the electrode, with the cannulation channel being defined by the sleeve.

The second side of the elongated body may be opposite the first side.

The elongated body may include a chain of body sections, with at least some of the body sections include tapered ends along a longitudinal axis of each of the at least some of the body sections, and with each of the plurality of electrode contacts being disposed at a respective different one of the body sections.

The elongated body may include a leading tip with an average width larger than a maximum body width of a remainder of the elongated body.

The cannulation channel may terminate at a reinforced area of a leading tip of the elongated body such that the cannulation channel is configured to cause the elongated body to be pulled into place from the leading tip using the guiding mechanism.

The cannulation channel may be configured to receive irrigation fluids dispensed through a perforated end located near a leading tip of the elongated body.

The device may further include an adapter fitted at an operator-end of the guiding mechanism, the adapter configured to at least direct the irrigation fluids from a fluid source for delivery via the cannulation channel. The adapter may include a luer-lock.

The guiding mechanism may include a guidewire defining an internal channel between the guidewire and internal walls defining the cannulation channel, with the internal channel being configured to receive irrigation fluids dispensed through a perforated end located near a leading tip of the elongated body.

The electrode may further include a radiopaque identifier element disposed proximate a leading tip of the elongated body.

The elongated body may include an elongated silicon-based elastomer body.

Each of the plurality of electrode contacts may include one or more of, for example, a stainless-steel contact and/or a platinum contact.

The electrode may include multiple folded electrode strips defining the elongated body, with the multiple folded electrode strip configured to be unfolded for deployment over the target area inside the body of the patient.

The target area may be a brain of the patient.

In some variations, an electrode is provided that includes an elongated body, a plurality of electrode contacts disposed on a first side of the elongated body, and a cannulation channel defined along a longitudinal axis of the elongated body. The cannulation channel is configured to receive a guiding mechanism to guide the electrode for placement at a target area inside a body of the patient.

Embodiments of the electrode may include at least some of the features described in the present disclosure, including at least some of the features described above in relation to the device, as well as one or more of the following features.

The cannulation channel may be defined within one of, for example, the elongated body, or a sleeve disposed on a second side of the elongated body.

The elongated body may include a chain of body sections, with at least some of the body sections including tapered ends along a longitudinal axis of each of the at least some of the body sections, and with each of the plurality of electrode contacts being disposed at a respective different one of the body sections.

The elongated body may include a leading tip with an average width larger than a maximum body width of a remainder of the elongated body.

The electrode may further include multiple folded electrode strips defining the elongated body, the multiple folded electrode strips configured to be unfolded for deployment over the target area inside the body of the patient.

In some variations, a method is provided that includes forming a hole to access an internal target area inside a body of a patient, coupling a guiding mechanism to an electrode comprising an elongated body and a plurality of electrode contacts disposed on a first side of the elongated body, and guiding the electrode, using the guiding mechanism, through the hole for placement at the target area inside the body of the patient.

Embodiments of the method may include at least some of the features described in the present disclosure, including at least some of the features described above in relation to the device and the electrode, as well as one or more of the following features.

Coupling the guiding mechanism to the electrode may include inserting the guiding mechanism through a cannulation channel defined along a longitudinal axis of the elongated body of the electrode.

Inserting the guiding mechanism through the cannulation channel may include one of, for example, inserting the guiding mechanism to the cannulation channel defined within the elongated body, or inserting the guiding mechanism to the cannulation channel defined in a sleeve disposed on a second side of the elongated body.

The method may further include subsequent to placement of the electrode, repeating the coupling and guiding for one or more other electrodes for placement of the one or more other electrode at respective locations.

Guiding the electrode may further include delivering irrigation fluid via the cannulation channel, the irrigation fluids being dispensed through one or more irrigation openings in the elongated body.

The electrode may include multiple folded electrode strips defining the elongated body, and the method may further include unfolding the multiple folded electrode strips defining the elongated body to deploy the unfolded electrode strips over the target area inside the body of the patient.

Other features and advantages of the invention are apparent from the following description, and from the claims.

BRIEF DESCRIPTION OF THE DRAWINGS

These and other aspects will now be described in detail with reference to the following drawings.

Like reference symbols in the various drawings indicate like elements.

DESCRIPTION

Disclosed herein are methods, systems, devices, and other implementations to place a subdural electrode array through a small drill hole in the skull using a guide mechanism, such as molded and flexible catheters, to navigate the electrodes into position. The implementations described herein include a device that includes an electrode comprising an elongated body, a plurality of electrode contacts disposed on a first side of the elongated body, and a cannulation channel defined along a longitudinal axis of the electrode, and a guiding mechanism received within the cannulation channel, with the guiding mechanism configured to guide the electrode for placement at a target area inside a body of a patient. The implementations also include an electrode comprising an elongated body, a plurality of electrode contacts disposed on a first side of the elongated body, and a cannulation channel defined along a longitudinal axis of the elongated body, the cannulation channel configured to receive a guiding mechanism to guide the electrode for placement at a target area inside a body of the patient. The implementations described herein further include a method including forming a hole to access an internal target area inside a body of a patient, coupling a guiding mechanism to an electrode comprising an elongated body and a plurality of electrode contacts disposed on a first side of the elongated body, and guiding the electrode, using the guiding mechanism, through the hole for placement at the target area inside the body of the patient.

Figure 1:
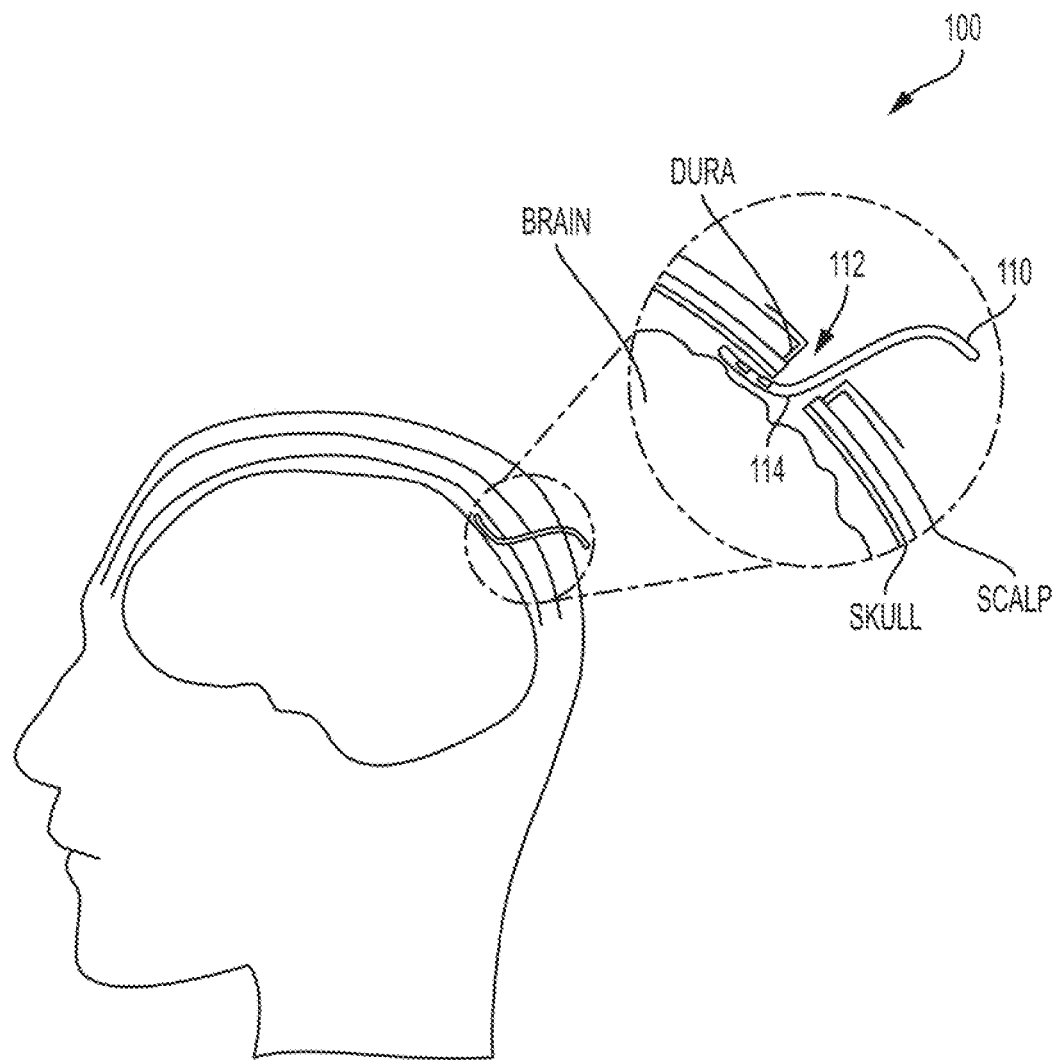
FIG. 1 is a diagram of a subdural electrode placement procedure performed through minimal bone exposure.

For example, FIG. 1 is a diagram 100 illustrating subdural electrode placement procedure performed through minimal bone exposure (burr-hole craniectomy). As illustrated, in order to achieve such minimal bone exposure, electrodes to be deployed on brain tissue (such as the schematically depicted flexible electrode 110) have to navigate acute angled paths/trajectories in order to allow placement of such an electrode tangential to the brain surface. For example, once an opening or hole 112 is formed, the electrode array 110 is configured to be bent so that its elongated body defines an acute angle (at a location 114 on the electrode 110, in the example of FIG. 1), which may be 70-90°. The structure of the electrode used may be configured to be bent to form angled sections over any angular range.

As will be described in greater detail below, the implementations described herein include use of cannulated subdural electrodes. Cannulation allows for guidance by, for example, a molded introducer catheter. The catheter allows for irrigation at the tip of the electrode to lubricate its passage. The moldable nature of catheters will allow for navigation of the electrode around the angles that currently limit electrode placement. Alternate embodiments include any catheter guided or cannulated subdural electrode, including strips or grids that could unfold or spread out in the subdural space. Alternate embodiments also include subdural electrodes used for uses other than epilepsy, including cortical stimulators and cyberprostheses. In those situations, the electrodes may be placed as part of a permanent prosthesis and not just for temporary monitoring. The electrodes described herein, and the procedures, systems, and apparatus for placing such electrodes, may also be used for other medical conditions in relation to other organs or parts of the body.

In some implementations, the electrode may be constructed from Silastic® (a product of Dow Corning Corporation, Midland, Mich.) with stainless steel contacts or platinum contacts. The leading tip of the electrode is generally broad to prevent twisting during insertion. The body of the electrode may taper (e.g., to a width of 3 mm) so as to allow placement of multiple (8 or more) electrodes through a small drill-hole. As will be discussed in greater detail below, a cannulation channel runs along the back side (noncontact side) of the electrode that can accommodate a catheter ranging, for example, from 3-5 French in size (1-1.67 mm outer diameter). The end of the cannulation channel at the tip of the electrode has a small channel that can direct irrigation from the cannulation to the electrode tip surface. The width of the electrode may be tapered between contacts in order to increase flexibility.

Figure 2A:
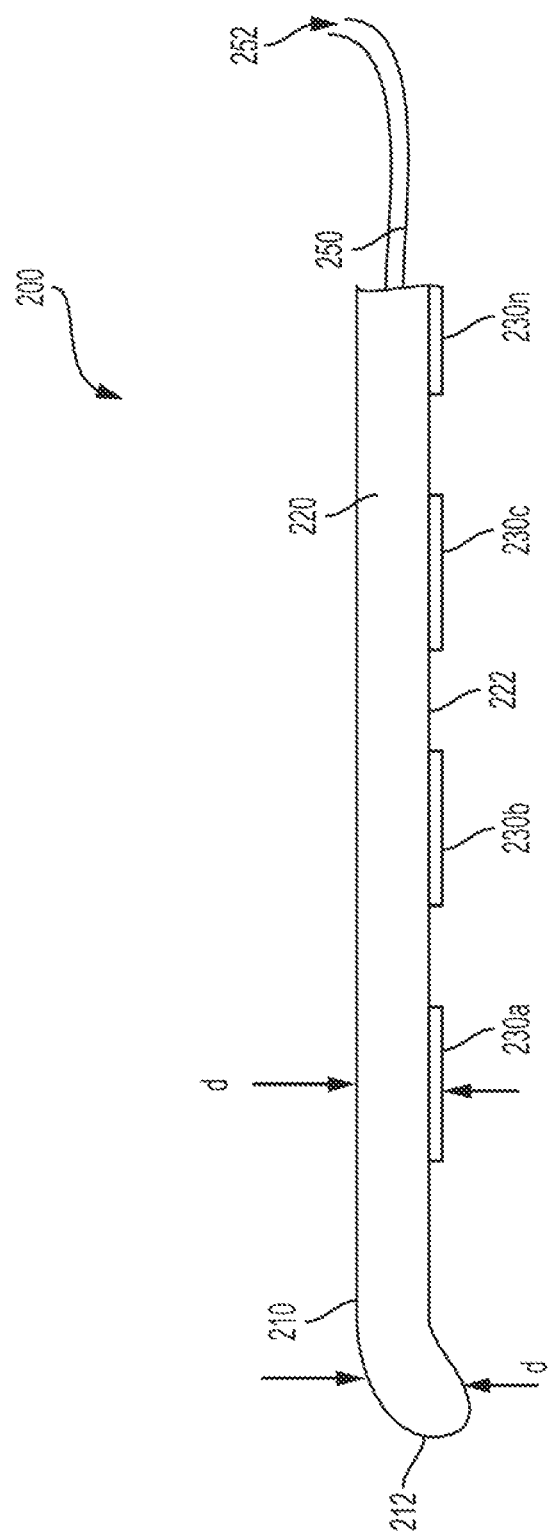
FIG. 2A is a side-view diagram of a cannulated subdural electrode that includes a guidewire/catheter entry point, and brain surface electrode contacts.

More particularly, with reference next to FIG. 2A, a diagram of a side view of a device 200 to facilitate deployment of electrodes within interior spaces inside a person's body, such as within a subdural space of a person, is shown. The device 200 includes an electrode 210 comprising an elongated body 220, with a plurality of electrode contacts 230a-n disposed on a first side 222 of the elongated body 220 (e.g., with n being 2, 3, 4, 8, or any other number of electrodes; generally, the number of contacts varies between 4-12). In some embodiments, the electrode may have only one (1) electrode contact. In some embodiments, the elongated body may be substantially flat (e.g., a strip-like structure), with a thickness, d, of dimensions 1-2 mm. Extending from each of electrodes 230a-n is a respective one of electrical wires 232a-n (shown in FIG. 2B) that can carry measured signals (representative of electrical activity within a brain, or of some other physiological activity with a target area where the electrode is deployed), and may also deliver electrical signal from an electrical source (e.g. a controller in communication with the various electrodes) to control the electrodes or to deliver electrical stimulation to the target area. In some embodiments, electrical signals may be communicated to and from the electrodes via a wireless interface (e.g., a UHF-based transceiver, such as UHF transceivers implemented in passive RFID devices, to allow electrical operation of the devices using power harvested from wireless signals; such wireless transceivers may be configured to operate in other RF bands). In such embodiments, wired electrical connections, such as the wired connections realized using the electrical wires 232a-n, may not be needed. In some examples, the electrodes 230a-n may be rectangular electrodes (or other electrode types and geometries) with dimensions, for example, of approximately 2.75 mm×4.57 mm (such dimensions can be used as to provide approximately the same contact area as a 4 mm round electrode, but the rectangular contact will have a narrower profile). The contacts may be spaced every 10 mm, or some other appropriate distance. The number of contacts per electrode can vary from 4 up to 12 and possibly more. The wire extending from an electrode is as small as possible (1.1 mm). The wires may have unique color codes, and may also include radio-opaque unique identifiers that allow for identification on x-ray.

Figure 2B:
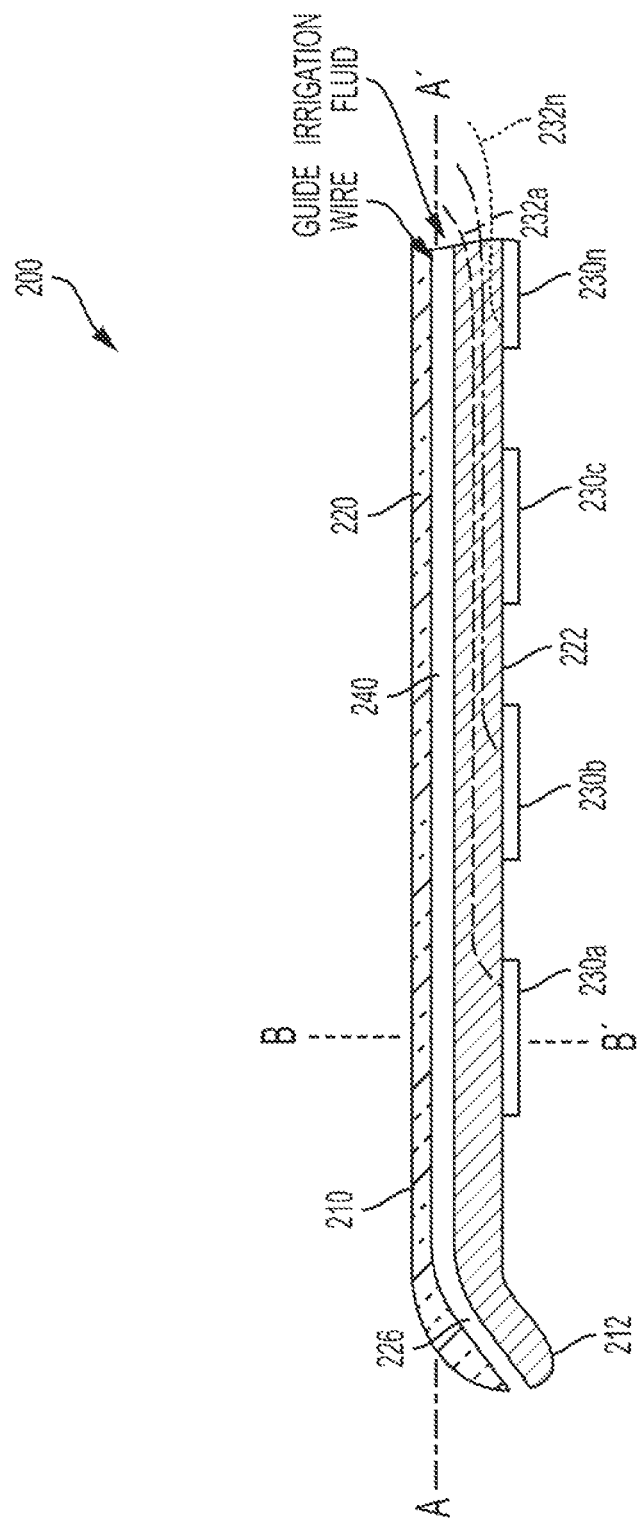
FIG. 2B is a lengthwise cross-section diagram of the cannulated subdural electrode of FIG. 2A.

As shown with further reference to FIG. 2B, providing a lengthwise cross-section diagram of the cannulated subdural electrode of FIG. 2A, the electrode 210 further includes a cannulation channel 240 defined along a longitudinal axis of the electrode 210. In the example implementations of FIGS. 2A and 2B, the cannulation channel 240 is defined within the elongated body 220, e.g., the elongated body 220 includes an internal channel that is contained within the elongated body 220. However, in some embodiments, the cannulation channel may be provided as the internal channel of a sleeve that is disposed as a different part on a second side (opposite the first side 222 on which the electrodes 230a-n are disposed) of the elongated body 220 (the sleeve, not shown in FIG. 2A or 2B, may extend integrally from the elongated body 220, or may be coupled in some manner to the elongated body 220). The cannulation channel 240, be it a cannulation channel defined within the elongated body 220 or a channel defined within a separate sleeve, is configured to receive a guiding mechanism 250, such as a catheter, a guidewire, or any other actuatable mechanism configured to be fitted inside the cannulation channel 240 to guide the electrode 210 for placement at a target area inside a body of a patient, and to be withdrawn upon deployment of the electrode at the target. In some variations, the cannulation channel may terminate at a reinforced area of a leading tip 212 of the elongated body 220, with the reinforced area configured to facilitate causing the elongated body to be pulled into place from the leading tip using a guidewire or a catheter.

In some embodiments, the elongated body 220 (and/or a sleeve coupled thereto) may be made from a flexible material, such as a plastic polymer (e.g., polyurethane), elastomers (e.g., silicone elastomers such as Silastic®), etc. The elongated body 220 of the electrode 210 (and/or a cannulation sleeve that may be attached thereto in some embodiments) may be produced via, for example, an extrusion process, or a molding process (with the resultant structure comprising the internal space defining the cannulation channel). Upon formation of the elongated body structure, electrical contacts, such as the electrical contacts 230a-n, may be placed on one side of the elongated body. In embodiments in which a cannulation sleeve is disposed on a second side of the elongated body, the elongated body and the cannulation sleeve may be produced as separate parts that are then attached to each other (through a bonding process, such as gluing, thermal bonding, etc.)

As noted, the device 200 further includes a guiding mechanism, such as the guiding mechanism 250 depicted in FIG. 2A, which may include a catheter or some other guiding mechanism (e.g., guidewire). The guiding mechanism is configured to be received within a cannulation channel, such as the cannulation channel 240 depicted in FIG. 2B, when an electrode (e.g., 210) is to be placed within a target area inside a body of a patient. In some implementations, the guidewire or catheter may be constructed from Silastic®, have a size of 3-5 French gauge, and be approximately 20 cm in length. The operator end of the guiding mechanism terminates in an adapter, such as luer-lock, that allows use of a syringe to both irrigate and rotate the catheter if necessary. A separate controlling instrument may be coupled to the operator end of the guiding mechanism, and may be configured to be controlled so as to actuate the leading end of the catheter to control its movement (i.e., to change its direction so as to negotiate sharp corners and change its trajectory en route to the destination location for the electrode). Examples of catheters that may be used in conjunction with the implementations described herein include the Stryker Excelsior catheters. Other types of catheters may also be used. In some examples, about 10 mm of the catheter tip may be firm and molded into an angle appropriate to facilitate passing the electrode over the surface of the target area (e.g., the brain) through a small drill hole. The remainder of the guiding mechanism (e.g., catheter) may be flexible. The guiding mechanism may be constructed from a radiopaque material (such as radiopaque polyurethane) that is visible through various radio imaging technologies (e.g., x-rays) in order to determine the location of the guiding mechanism within a body of a patient. In some implementations, the guiding mechanism (be it a catheter, guidewire, or some other type guide mechanism) may be equipped with one or more fiber optical wires that attach to a light-capture device (e.g., camera). A light source may deliver light signals via one such optical fiber, whose end is located near the leading end of the catheter, to illuminate the area through which the catheter (and thus the electrode) is advancing, while another fiber optical wire may deliver reflected light back to the light-capture device, via a lens assembly, to allow the operator to view the area where the electrode is located. In some embodiments, the optical fibers may be separately fitted through the cannulation channel rather than being part of the catheter device or assembly.

Figure 5:
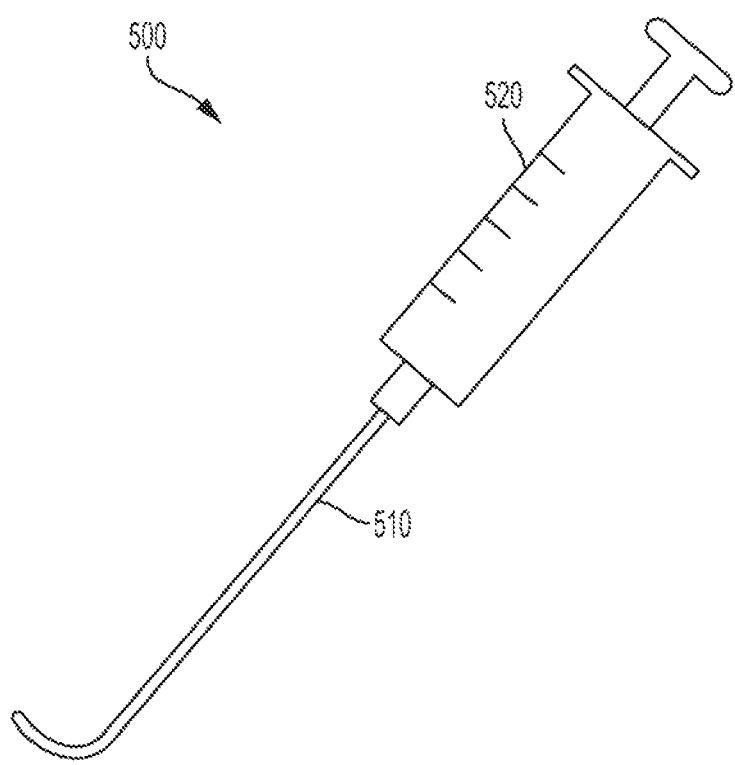
FIG. 5 is a schematic diagram of an implementation comprising a catheter and a syringe to introduce irrigation fluid into an inner channel defined in the catheter.

In embodiments in which the guiding mechanism comprises a catheter, such a catheter may be a tube that defines an internal channel through which irrigation fluid can pass and be delivered to irrigate the area surrounding the progressing structure (e.g., the electrode 210 of FIGS. 2A and 2B). For example, and as illustrated in FIG. 2B, an irrigation channel 226 may be defined at a distal end of the elongated body 220. Irrigation fluid introduced into the inner channel of the catheter can exit at one or more perforations or openings located at an end of the catheter that is placed near the elongated body's distal end (by passing the catheter through the cannulation channel 240). In the example of FIG. 2A, the catheter or guidewire is shown to have a distal opening 252 through which irrigation fluid (introduced, for example, using a syringe), may pass, and exit via the irrigation channel 226 to the area around the electrode. For example, FIG. 5 is a schematic diagram of an implementation 500 comprising a catheter 510 (which may be similar to the catheter 250 of FIG. 2A) and a syringe 520 to introduce irrigation fluid into an inner channel in the catheter. The catheter 510 is configured to be received in a cannulation channel (such as the cannulation channel 240 of FIG. 2B) during electrode placement. The catheter/guidewire may be implemented with an angled tip to allow the catheter, and thus the electrode, to navigate the acute angled paths illustrated, for example, in FIG. 1. The syringe 520 allows for irrigation to be directed through the cannulation channel, and out at the electrode tip (e.g., via the cannulation channel 226 of FIG. 2B), thus lubricating the surface of the target area (e.g., brain), and the path thereto, during placement of the electrode. In some embodiments, a multi-perforated catheter may be used that includes multiple perforations (e.g., located at a distal/leading tip of the catheter) to irrigate the areas through which the electrode (e.g., the array 210 of FIG. 2) passes. Irrigations fluids may thus flow (under pressure delivered by an external syringe or pump) through the irrigation perforation(s), and then through channels or perforations defined between the cannulation channel (e.g., the channel 240) and extending to the side of the elongated body on which the electrical contacts (e.g., 230a-n) are disposed.

Figure 6:
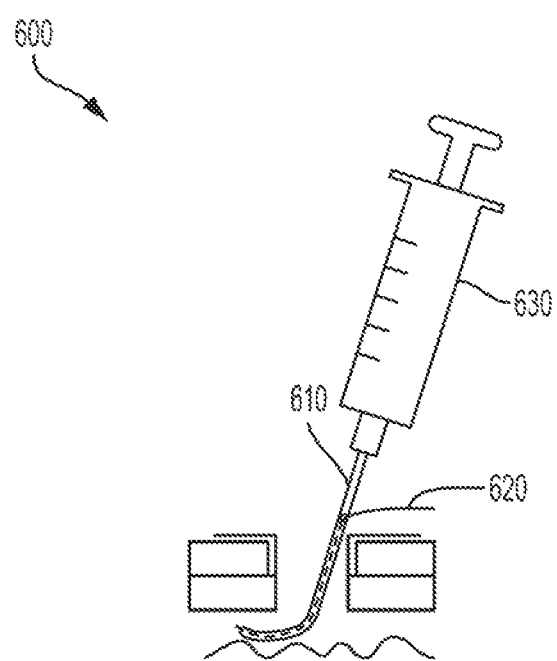
FIG. 6 is a schematic diagram illustrating electrode placement procedure using an angled-tip catheter.

FIG. 6 is a diagram of another example implementation of a system 600 for placing electrodes in the subdural space. In this example, the guiding mechanism used is a specially designed angled-tip catheter 610 that facilitates navigating an electrode at an acute angle under the skull edge. As shown in FIG. 6, the angled-tip catheter is coupled to an electrode 620 by, for example, inserting the leading end of the angled-tip catheter 610 (the leading end may have a single or multiple irrigation perforations) into the cannulation channel of the electrode. Irrigation fluid may be introduced into an internal channel in the catheter 610 using a syringe 630 that is coupled to the opening of the catheter 610 via an adapter (not shown) such as a luer-lock.

In various examples, the guiding mechanism may not have its own internal channel, and instead, irrigation fluid may flow in a channel defined between the body of the guiding mechanism (e.g., guidewire) and the interior walls of the cannulation channel. Here too, the irrigation fluid may exit the cannulation channel through one or more perforations or openings in the cannulation channel, and be directed to the area to be irrigated via irrigation channels defined in the elongated body 220, including the irrigation channel 226 depicted in FIG. 2B.

Figure 3A:
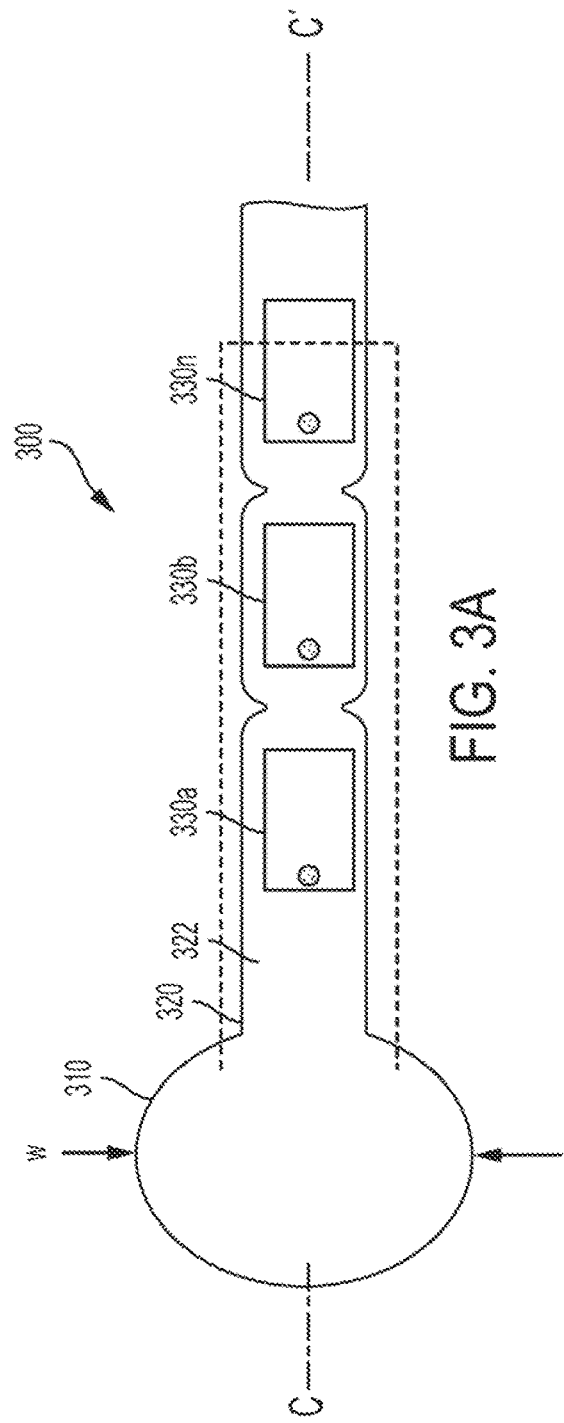
FIG. 3A is a diagram of an inferior surface of a cannulated subdural electrode with electrode contacts.

With reference next to FIG. 3A, a diagram showing a bottom view of a cannulated subdural electrode 300, which may be similar to the electrode 210 of FIGS. 2A-B, is provided. The electrode 300 comprises a plurality of electrical contacts 330a-n disposed on a surface 322 (e.g., the tissue-facing surface, also referred to as the contact surface) of an elongated body 320 (which may be similar to the elongated body 220). As also discussed in relation to the electrode 210 of FIGS. 2A-B, here too, the electrical contacts 330a-n may be rectangular electrodes (or other electrode types and geometries) with dimensions, for example, of approximately 2.75 mm×4.57 mm. The contacts may be disposed on the surface 322 at uniform spacing from each other (e.g., spaced every 10 mm). The number of contacts per electrode can vary from 4 up to 12, and may possibly be outside this range. Each of the electrical contacts may be identifiable through using a radio-opaque identifier (so that it can be easily recognized using different imaging technologies such as x-ray imaging, CAT imaging, etc.) Such identifiers may be numbered identifiers, or other alphanumerical identifiers. In embodiments in which the electrical contacts are connected to a central controller (such as the controller 920 illustrated in FIG. 9), configured to receive and process measurements performed by the electrical contacts or to send electrical signals to the electrical contacts, the wires used may have a gauge of, for example, 1.1 mm. The wires may have unique color codes (to facilitate placement of the electrodes and wiring). As noted, in some embodiments, the electrical contacts may include wireless communication circuitry adapted to establish wireless communication with the central controller through which identification information and electrical signaling may be communicated.

Figure 3B:
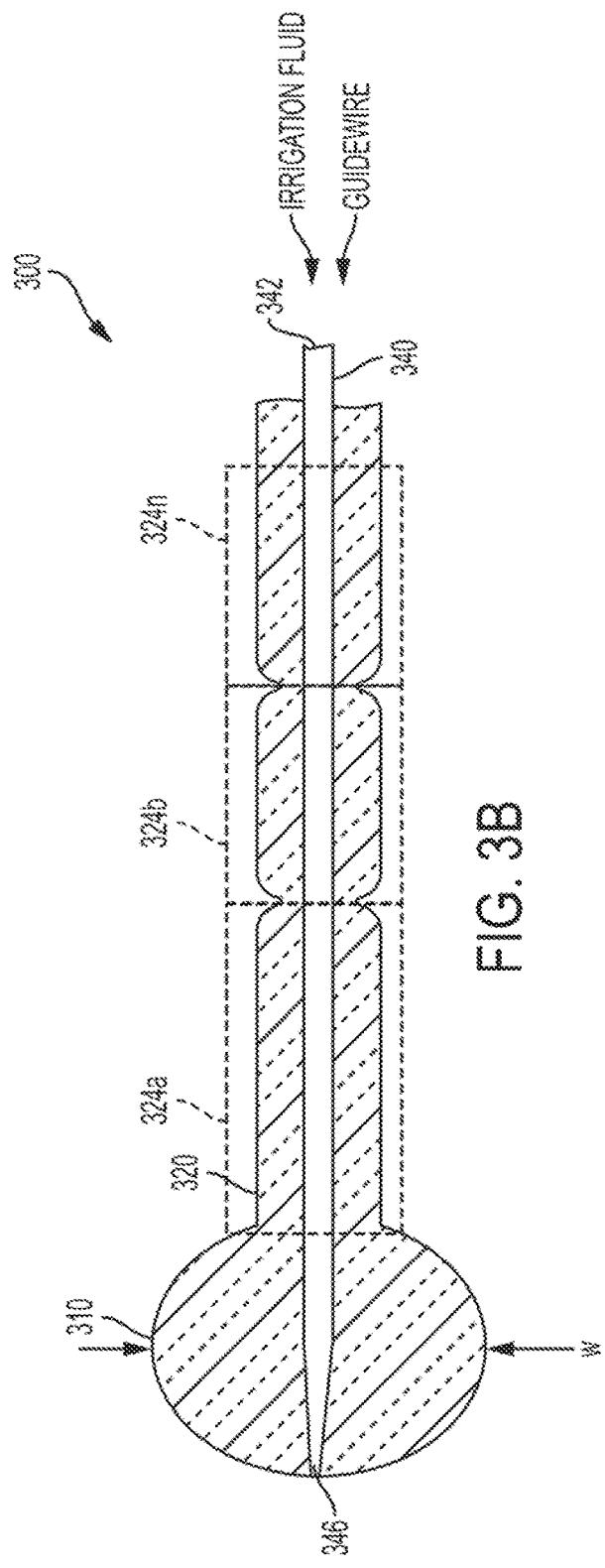
FIG. 3B is a width-wise cross-sectional diagram of the cannulated subdural electrode of FIG. 3A.

As further shown in FIG. 3A, and with reference also to FIG. 3B, providing a width-wise cross-sectional diagram of the cannulated subdural electrode 300 of FIG. 3A, the electrode 300 includes a distal (leading) tip 310 with an average width larger than a maximum body width of a remainder of the elongated body 320. In the examples of FIGS. 3A-B, the minimum width of the leading tip 310 is greater than the maximum width of the rest of the elongated body 320 of the electrode 300 (the maximum width of the leading tip is denoted using the arrow marking a width, W, at around the half-way point of the tip 310). The larger width of the leading tip (in some embodiments, the leading tip may be significant wider than the remainder part of the elongated body) allow the electrode to resist/reduce twisting or folding during placement of the electrode. In some embodiments, a radiopaque identifier element may be disposed proximate to the leading tip 310 of the elongated body to allow tracking of the location of the electrode while it is being maneuvered to its destination location. As illustrated in FIGS. 3A-B, in some implementations, the electrode 300 is tapered between contacts to increase flexibility. Thus, in such embodiments, the elongated body 320 may include a chain of body sections 324a-n, with at least some of the body sections including tapered ends along a longitudinal axis of electrode, and with each of the plurality of electrodes being disposed at a respective different one of the body sections 324a-n.

As additionally shown in FIG. 3B, a cannulation channel 340, which may be similarly structured to the cannulation channel 240 of FIGS. 2A-B, is defined within the elongated body 320 of the electrode 300. The cannulation channel 340 is configured to receive a guiding mechanism (a catheter or guidewire) that is placed via an entry opening 342 of the electrode 300, and can be pushed substantially to the leading tip 310 of the electrode 300. As with the electrode 210 of FIGS. 2A-B, irrigation fluid can be delivered via an internal channel in the catheter or guidewire, or via through the space defined between the internal walls of the cannulation channel 340 and the exterior of the catheter/guidewire received within the cannulation channel 340. In some implementations, the cannulation channel 340 may be tapered at the tip to allow passage of irrigation fluid while confining the catheter or guidewire (e.g., the catheter or guidewire may have a diameter larger than the diameter of the distal opening 346 of the cannulation channel 340 located at around the leading tip 310).

As noted herein, in some embodiments, the elongated body of an electrode may taper (e.g., to a width of 3 mm) in order to allow placement of multiple electrodes (to form an electrode array) through a single drill hole formed in the skull (or some other area of the body of the patient). To further facilitate deployment of multiple electrodes through a single drill hole, in some implementation, an electrode inserted through a drill hole may comprises multiple folded electrode strips that define the elongated body. The multiple folded electrode strips are configured to be unfolded for deployment over a target area within the body. Thus, a guiding mechanism may be fitted within a cannulation channel defined for such a folded electrode (the folded electrode may be associated with a single cannulation channel, rather than have individual cannulation channel for each of the folded electrode strips). Upon reaching the destination location (through actuation of the guiding mechanism to navigate the folded electrode), the guiding mechanism may further be configured to be actuated so as to cause the unfolding of the individual folded electrode strips (e.g., by releasing a latch that maintains the electrodes in a folded array, and then causing a rolling motion to unspool or unfold the electrode strips). As also noted herein, target areas where the electrodes described herein may be deployed may include, in addition to a patient's brain, other hard to reach areas of the body (e.g., the gastrointestinal system). Furthermore, the electrodes described herein may also be used as cortical stimulators and cyberprostheses. In these situations, the electrodes may be placed as part of a permanent prosthesis and not just for temporary monitoring and/or stimulation.

Figure 4A:
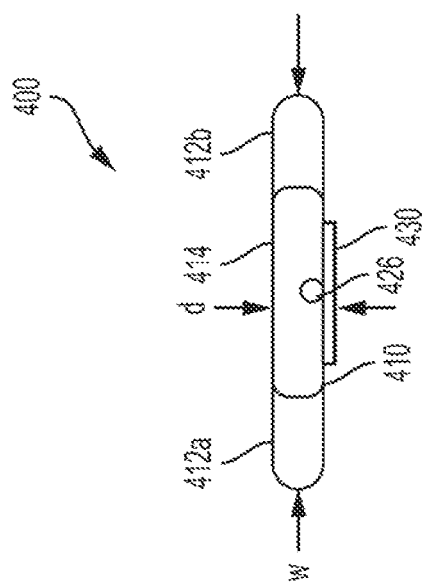
FIG. 4A is a transverse cross-sectional diagram of catheter tip of the electrode of FIGS. 2A-B or 3A-B.

With reference to FIG. 4A, a cross sectional diagram 400 of a leading tip 410 (which may be similar to the tip 310) of an electrode (such as the electrode 210 of FIG. 2A-B or 300 of FIGS. 3A-B). The diagram illustrates the structure of the leading tip 410 that includes the wide portions 412a-b, having a length of W, that are wider than the maximum width of the rest of the elongated body (whose end area, at the leading tip 410, is marked as end 414). The leading tip 410 also includes the opening 426 of a cannulation channel. As noted the cannulation channel tapers or narrows at an area proximate to the leading tip to allow irrigation fluid delivered through the cannulation channel extending along the elongated body (as illustrated by the cannulation channel 240 of FIG. 2) to be dispensed to the area being traversed by the electrode (e.g., as it is being guided via actuation of the catheter or guidewire), while preventing or inhibiting the catheter/guidewire (which has a diameter larger than the diameter of at least the opening 426) from being protruded or extending via the opening 426. The diagram 400 further shows a side of the nearest electrode contact 430 (i.e., nearest to the leading tip) disposed on the contact surface of the elongated body. As shown, the thickness of the electrode, from the bottom surface of the electrode contact 430, to the non-contact surface of the elongated body 410 of the electrode is marked as d, (similar to the thickness of the electrode 210 of FIG. 2A).

Figure 4B:
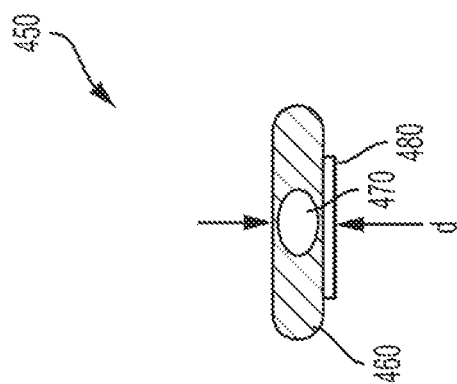
FIG. 4B is a transverse cross-sectional diagram of a body of an electrode.

FIG. 4B is a transverse cross-sectional diagram 450 of a body 460 (similar to the bodies 210 or 300) of an electrode (such as the electrodes depicted in FIGS. 2A-B and 3A-B). Thus, the cross-sectional diagram 450 illustrates the structure that would be seen if the elongated body was transversely cut (e.g., along the line B-B depicted in FIG. 2B), and viewed from the side towards the location of the cut. As shown, the cut section of the elongated body 460 includes a cannulation channel 470 defined within the body 460 (similarly to the cannulation channel 240 of FIG. 2B). Also shown in FIG. 4B is a side of an electrode contact 480 nearest to the location of the transverse cut depicted in FIG. 4B. For example, if the transverse cut shown in FIG. 4B was made in the elongated body 210 of FIGS. 2A-B at a location between the electrode contacts 330a and 330b, the electrode 480 would correspond to the electrode contact 330a (or 230a) when the transverse cut is being viewed in a direction towards the leading tip of the elongated body. Here too, the distance d, between the two arrows provided in FIG. 4B, corresponds to the thickness of the electrode from the bottom surface of the electrode contact 480 to the non-contact surface of the elongated body of the electrode.

Figure 7:
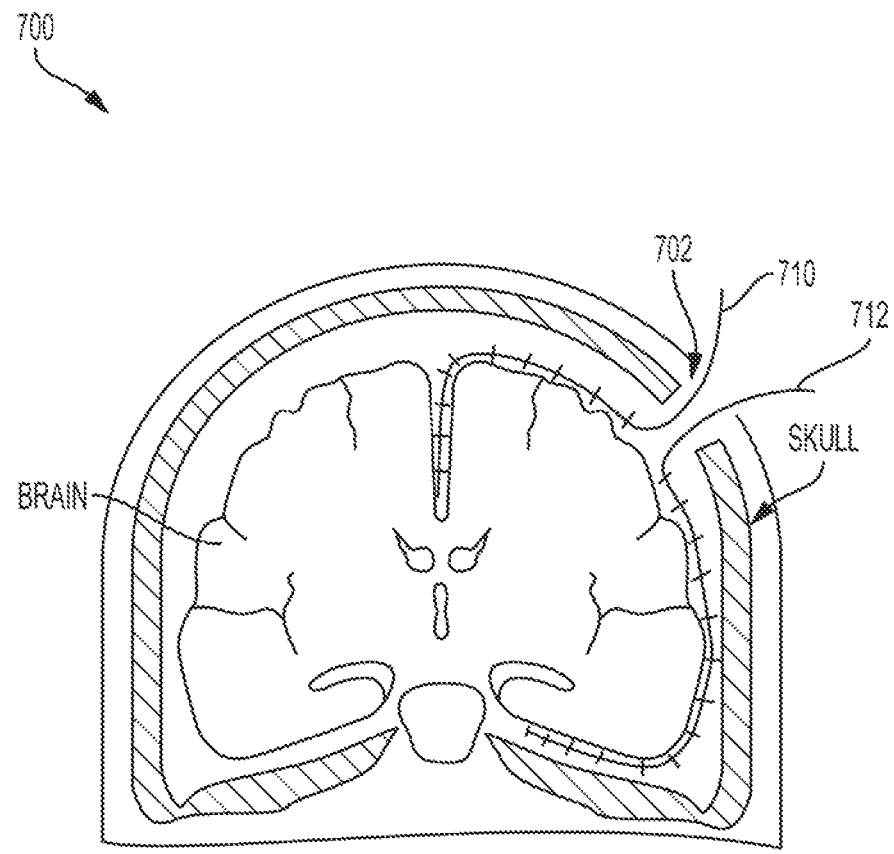
FIG. 7 is a diagram of electrodes, such as the electrodes of FIGS. 2A-4B, being placed in a subdural space of a patient's brain.

With reference next to FIG. 7, a diagram of an electrode array (comprising electrodes such as the electrodes of FIGS. 2A-5) placed in a subdural space of a patient's brain is shown. A guiding mechanism, such as a catheter or guidewire (such as the catheter/guidewire 250 of FIG. 2A, or the catheters/guidewires 510 and 610 of FIGS. 5 and 6) may be used to navigate the cannulated electrodes around angles distant from the entry point. The guiding mechanism used is fitted through cannulation channels of the respective electrodes, and guides (e.g., through actuation/manipulation of a controlling actuator of the guide mechanism) such electrodes through acute angles to their destination locations within the target area. Once a particular electrode has been placed at its destination, the catheter can be withdrawn (retracted) from the cannulation channel of that electrode, and fitted into another electrode, which is then guided, via the same bore hole 702 made in the skull (through which the previous electrode was guided to its destination) to the destination for the current electrode. In FIG. 7, electrodes 710 and 712 are shown making acute angles in the subdural space to allow coverage of the interhemispheric fissure and inferior brain surface.

More particularly, the process for placement of an electrode at hard-to-reach locations of the target array (e.g., the subdural space in the example of FIG. 7) is as follows. A 3-4 cm incision is generally made over the area of interest. A high-speed drill can be used to create a drill hole 15-20 mm in diameter. After hemostasis is obtained the dura is opened in a stellate fashion. A guide catheter is placed into an electrode and is carefully placed under the dural edge and advanced with the guide catheter while gently irrigating (as noted, the electrode being advanced may include multiple folded electrodes). The guiding catheter/guidewire is then removed, and is placed in the next electrode to be placed. This can be done with a large number of electrodes circumferentially around the drill hole. Intraoperative x-ray or fluoroscopy may be used to verify good placement. The leads are then tunneled out the skin surrounding the incision. The drill hole is then sealed with a polymer sealant such as Duraseal™ or a silastic burr hole cover so as to minimize the risk of cerebrospinal fluid leakage through the tunneling sites. Advantages of performing this procedure using the electrodes and devices described herein include the fact that a subdural array placed without craniotomy through a small drill hole would combine the favorable aspects of existing approaches, allowing good coverage of the cortex (where most seizures arise) while avoiding the invasiveness and risk of craniotomy. As noted, the approaches and devices (e.g., the cannulated subdural electrodes) described herein advantageously allow for use of a guide catheter whose tip can be molded into an appropriate angle to provide force tangential to the brain surface during placement. Also, the electrode is not pushed into position at its base but pulled into position by the catheter in the tip. Therefore, there is no need for the broad, flat design anywhere except the tip. The electrode can be narrow at the base, allowing for placement of an electrode array that can cover the brain in a radial fashion from one small drill hole. Other electrode deployment configurations (such as the configuration depicted in FIG. 7) may be realized. As noted, the guiding catheter/guidewire can also allow irrigation through perforations in the tip during placement to reduce the risk of brain injury. A molded catheters can not only help guide the electrode onto the brain surface initially, but also can help electrodes change direction intracranially. This aids in covering hard to access regions like the interhemispheric fissure and inferior brain surface.

Figure 8:
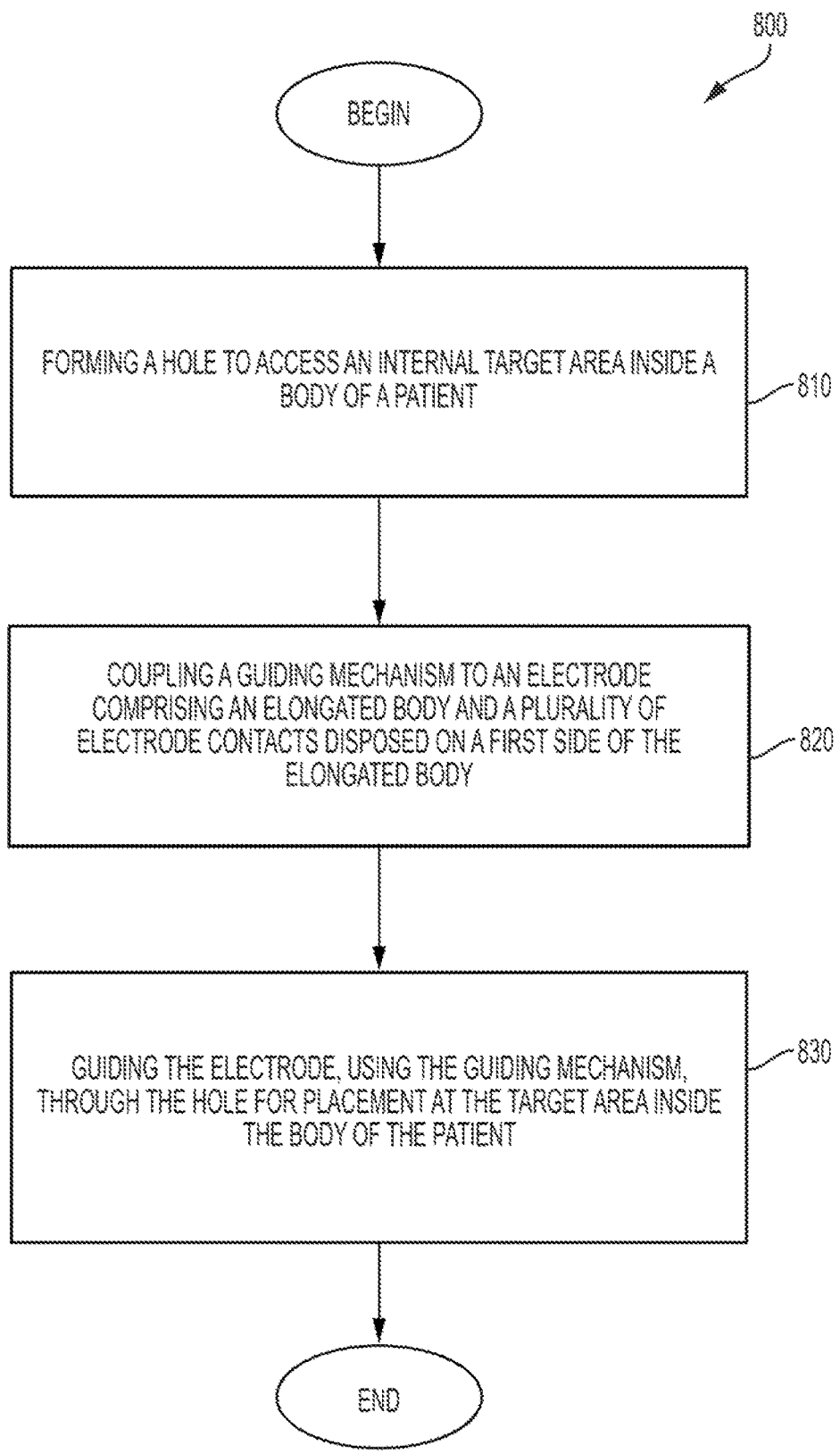
FIG. 8 is a flowchart of an example procedure to place electrodes.

With reference to FIG. 8, a flowchart of an example procedure 800 to place electrodes, such as the electrodes described herein, in a target area, is shown. The procedure 800 may be similar, at least in part, to the procedure described in relation to FIG. 7. The procedure 800 includes forming 810 a hole (e.g., a drill hole) to access an internal target area inside a body of a patient. For example, as discussed herein, when the electrode is to be deployed in the subdural space of the patient's brain, a high-speed drill may be used to create a drill hole 15-20 mm in diameter in the skull.

Having created the drill hole through which electrodes can be introduced (e.g., into the subdural space), the procedure 800 further includes coupling 820 a guiding mechanism (e.g., a catheter or guidewire, such as those schematically depicted in FIGS. 2A, 5, and 6) to an electrode (such as those discussed in relation to FIGS. 2A-4B) comprising an elongated body and a plurality of electrode contacts disposed on a first side of the elongated body. The electrode contacts may be rectangular or round in shape, and may be constructed from stainless steel, platinum, or some other conductive material. In some embodiments, coupling the guiding mechanism to the electrode may include inserting the guiding mechanism through a cannulation channel defined along a longitudinal axis of the elongated body of the electrode. Inserting the guiding mechanism through the cannulation channel may include one of, for example, inserting the guiding mechanism to the cannulation channel defined within the elongated body, or inserting the guiding mechanism to the cannulation channel defined in a sleeve disposed on a second side of the elongated body.

In some embodiments, and as was illustrated in FIGS. 3A-B, the elongated body may include a chain of body sections, with at least some of the body sections including tapered ends along a longitudinal axis of each of the at least some of the body sections, and with each of the plurality of electrode contacts being disposed at a respective different one of the body sections. In some examples, the elongated body may include a leading tip with an average width larger than a maximum body width of a remainder of the elongated body.

With continued reference to FIG. 8, the procedure 800 additionally includes guiding 830 the electrode, using the guiding mechanism (fitted through the cannulated channel), through the hole for placement at the target area inside the body of the patient. Guiding the electrode may be achieved through actuation of the guiding mechanism. For example, mechanical actuations may be applied through rotating and pushing of the catheter to cause the far end to likewise be rotated and pushed in such a way that the guiding mechanism, and thus the electrode, can negotiate sharp corners. In some embodiments, the operator's end of the of the guiding mechanism may have a specialized user interface (e.g., handle) that causes, through manipulation of that user interface, delivery of resultant electrical or mechanical power that causes other parts of the guiding mechanism (including the distal end of the guiding mechanism) to be actuated in some particular manner.

In some implementations, the procedure may also include, subsequent to placement of the electrode, repeating the coupling and guiding for one or more other electrodes for placement of the one or more other electrodes at respective one or more other locations. Thus, through repetition of this procedure, multiple electrodes can be fitted and passed through a single, and relatively small, drill hole. Furthermore, such electrodes can be guided to remote parts of the target area (e.g., locations at the opposite end of the head from where a drill hole was initially formed). In some embodiments, guiding the electrode may further include delivering irrigation fluid via the cannulation channel, with the irrigation fluids being dispensed through irrigation openings in the elongated body. For example, irrigating fluid (which may be introduced via an adapter, such as a luer-lock) may pass directly through the cannulation channel (e.g., in the space between the guiding mechanism and the internal walls of the cannulation channel), or indirectly through the cannulation channel (e.g., via an internal channel defined within the guiding mechanism that has been received in the cannulation channel). It is noted that the adapter may also be used to actuate the guiding mechanism to facilitate the advancement of the guiding mechanism and an electrode coupled thereto, to the destination location. Where the irrigation fluid passes through the guiding mechanism (such as a catheter), the guiding mechanism will include one or more perforations or openings (typical at the distal end of the guiding mechanism) through which the irrigation fluid can be delivered. That irrigation fluid is then dispensed through openings or perforations in the elongated body.

As noted, in some examples, the electrode may include multiple folded electrode strips defining the elongated body. In such embodiments, the procedure 800 may further include unfolding the multiple folded electrode strips defining the elongated body to deploy the unfolded electrode strips over the target area inside the body of the patient. The unfolding can be performed by actuating the guiding mechanism to cause rolling of the folded electrode strip to thus cause the strips to unfold and be deployed over the target area.

Figure 9:
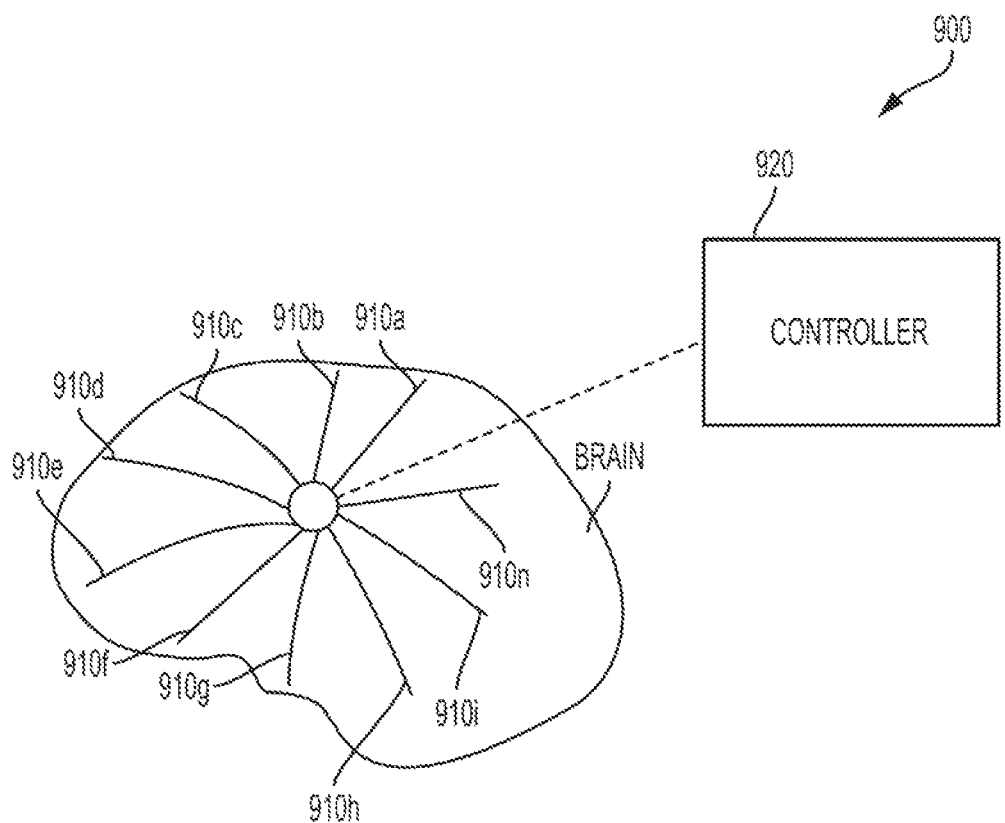
FIG. 9 is a diagram illustrating an example deployment of multiple electrodes.

Turning next to FIG. 9, a diagram 900 showing the resultant deployment of multiple electrodes 910*a-n* following performance of an electrode-placement procedure (such as the procedure 800 described in relation to FIG. 8) is provided. The placement of the multiple electrodes 910*a-n* can be achieved, in some embodiments, based on the narrow electrode profile that allows placement of multiple electrodes through a small skull opening. As illustrated in FIG. 9, the deployment of the multiple electrodes is based, in this example, on a radial scheme that is used to cover a large portion of the cerebral hemisphere using a small exposure. The particular deployment/distributive scheme that is used can be tailored to each individual patient, using, in each case, small exposure and multiple electrodes. Thus, any desired type of configuration (non-radial configuration, non-symmetrical configurations, etc.) may be used. The configuration used may be such where the electrodes are directed to various predetermined locations at the subdural space (or other locations within a body of a patient) for placement therein, with the tail end of the electrodes not necessarily being near the drill hole. That is, an electrode may be placed at a location where its tail end substantially far from the drill hole (and may be placed as far as the catheter, guidewire, or other guiding mechanism may reach inside the target area within the body of the patient). A controller 920 is in electrical communication with the electrode contacts on the multiple electrodes. Such electrical communication may be established, in some embodiments, via wired electrical connections, achieved using wires such as the wires 232*a-n* shown in FIG. 2B. Alternatively, the electrical communication between the controller 920 and the electrical contacts of the electrodes 910*a-n* can be performed using wireless communication, achieved using wireless transceivers included with the controller 920, and with the various electrical contacts disposed on the multiple electrodes (in some embodiments, one transceiver per electrode may be provided, with that transceiver then having direct electrical communication with the various electrode contacts on the respective electrode). The controller 920 is configured to collect measurements of electrical activities obtained through the electrode contacts, and/or to controllably send electrical signals (to cause electrical stimulation) to one or more of the electrode contacts. The controller 920 may also be configured to process signals it received, and/or communicate measurements it received to a remote device that performs further processing. In some embodiments, the controller 920 may be a processor-based controller, a state-machine controller, or any other type of controller. The controller 920 may also include a memory storage device to store data (e.g., measurement data collected from the various electrode contacts) and or programmable instructions to be executed on a processor, filtering circuitry (to filter our or suppress signals that may cause adverse effects to the patient), a communication module (such as a transceiver), a power source (e.g., to operate the controller's circuitry, and/or to transmit electrical stimulation signals to various electrode contacts), and other circuits, modules, and components to operate the controller 920.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A device comprising:
   a flexible electrode array comprising an elongated body having a length, a plurality of electrode contacts disposed on a substantially flat first side of the elongated body, and a cannulation channel defined along a longitudinal axis of the flexible electrode array, wherein the substantially flat first side of the elongated body extends along substantially the length of the elongated body; and a flexible guiding mechanism received within the cannulation channel, the flexible guiding mechanism configured to flexibly guide the flexible electrode array through acute angled paths or trajectories for placement tangential to tissue in a subdural space of a patient.

2. The device of claim 1, wherein the cannulation channel is defined within the elongated body.

3. The device of claim 1, further comprising a sleeve disposed on a second side of the elongated body of the flexible electrode array, wherein the cannulation channel is defined by the sleeve.

4. The device of claim 3, wherein the second side of the elongated body is opposite the first side.

5. The device of claim 1, wherein the elongated body comprises a chain of body sections, wherein at least some of the body sections include tapered ends along a longitudinal axis of each of the at least some of the body sections, and wherein each of the plurality of electrode contacts is disposed at a respective different one of the body sections.

6. The device of claim 1, wherein the elongated body comprises a leading tip with an average width larger than a maximum body width of a remainder of the elongated body.

7. The device of claim 1, wherein the cannulation channel terminates at a reinforced area of a leading tip of the elongated body such that the cannulation channel is configured to cause the elongated body to be pulled into place from the leading tip using the guiding mechanism.

8. The device of claim 1, wherein the cannulation channel is configured to receive irrigation fluids dispensed through a perforated end located near a leading tip of the elongated body.

9. The device of claim 8, further comprising an adapter fitted at an operator-end of the flexible guiding mechanism, the adapter configured to at least direct the irrigation fluids from a fluid source for delivery via the cannulation channel.

10. The device of claim 9, wherein the adapter comprises a luer-lock.

11. The device of claim 1, wherein the flexible guiding mechanism comprises a guidewire defining an internal channel between the guidewire and internal walls defining the cannulation channel, the internal channel configured to receive irrigation fluids dispensed through a perforated end located near a leading tip of the elongated body.

12. The device of claim 1, wherein the flexible electrode array further includes a radiopaque identifier element disposed proximate a leading tip of the elongated body.

13. The device of claim 1, wherein the elongated body comprises an elongated silicon-based elastomer body.

14. The device of claim 1, wherein each of the plurality of electrode contacts comprises one or more of: a stainless-steel contact, or a platinum contact.

15. The device of claim 1, wherein the flexible electrode array comprises multiple folded electrode strips defining the elongated body, the multiple folded electrode strip configured to be unfolded for deployment over the target area inside the body of the patient.

16. The device of claim 1, wherein the tissue in the subdural space is brain tissue of the patient.

17. The device of claim 1, wherein the cannulation channel is further configured to, during progression of the flexible electrode array to the tissue in the subdural space, deliver irrigation fluid via an irrigation fluid passage defined through one or more of:
a space defined between a body of the flexible guiding mechanism received within the cannulation channel and interior walls of the cannulation channel, or
an interior channel defined within the body of the flexible guiding mechanism received within the cannulation channel.

18. The device of claim 1, wherein the flexible guiding mechanism comprises an actuatable flexible guiding mechanism to cause the flexible electrode array, comprising the cannulation channel containing the actuatable flexible guiding mechanism to navigate the acute paths or trajectories in response to manipulation of the actuatable flexible guiding mechanism.

19. The device of claim 1, wherein each of the plurality of electrode contacts of the electrode array is configured to communicate with a controller through wired communication or wireless communication, and wherein the controller is configured to perform one or more of: collect measurements of electrical activities obtained through the plurality of electrode contacts, or controllably send to one or more of the plurality electrode contacts electrical signals to cause electrical stimulation to one or more locations of the tissue in the subdural space of the patient.

20. A flexible electrode array comprising:
an elongated body having a length and a substantially flat first side of the elongated body, the substantially flat first side of the elongated body extending along substantially the length of the elongated body;
a plurality of electrode contacts disposed on the substantially flat first side of the elongated body; and
a cannulation channel defined along a longitudinal axis of the elongated body, the cannulation channel configured to receive a flexible guiding mechanism to flexibly guide the flexible electrode array through acute angled paths or trajectories for placement tangential to tissue in a subdural space of a patient.

21. The flexible electrode array of claim 20, wherein the cannulation channel is defined within one of: the elongated body, or a sleeve disposed on a second side of the elongated body.

22. The flexible electrode array of claim 20, wherein the elongated body comprises a chain of body sections, wherein at least some of the body sections include tapered ends along a longitudinal axis of each of the at least some of the body sections, and wherein each of the plurality of electrode contacts is disposed at a respective different one of the body sections.

23. The flexible electrode array of claim 20, wherein the elongated body comprises a leading tip with an average width larger than a maximum body width of a remainder of the elongated body.

24. The flexible electrode array of claim 20, further comprising:
multiple folded electrode strips defining the elongated body, the multiple folded electrode strips configured to be unfolded for deployment over the target area inside the body of the patient.

25. A method comprising:
forming a hole to access target tissue in a subdural space of a patient;
coupling a flexible guiding mechanism to a flexible electrode array comprising an elongated body having a length and a plurality of electrode contacts disposed on a substantially flat first side of the elongated body, the substantially flat first side of the elongated body extending along substantially the length of the elongated body; and
flexibly guiding the flexible electrode array, using the flexible guiding mechanism, through the hole and through acute angled paths or trajectories for placement tangential to the tissue in the subdural space of the patient.

26. The method of claim 25, wherein coupling the guiding mechanism to the flexible electrode array comprises:
   inserting the flexible guiding mechanism through a cannulation channel defined along a longitudinal axis of the elongated body of the flexible electrode array.

27. The method of claim 26, wherein inserting the flexible guiding mechanism through the cannulation channel comprises one of:
   inserting the flexible guiding mechanism to the cannulation channel defined within the elongated body, or
   inserting the guiding mechanism to the cannulation channel defined in a sleeve disposed on a second side of the elongated body.

28. The method of claim 25, further comprising:
   subsequent to placement of the flexible electrode array, repeating the coupling and guiding for one or more other flexible electrode arrays for placement of the one or more other flexible electrode arrays at respective locations.

29. The method of claim 25, wherein the elongated body comprises a chain of body sections, wherein at least some of the body sections include tapered ends along a longitudinal axis of each of the at least some of the body sections, and wherein each of the plurality of electrode contacts is disposed at a respective different one of the body sections.

30. The method of claim 25, wherein the elongated body comprises a leading tip with an average width larger than a maximum body width of a remainder of the elongated body.

31. The method of claim 25, wherein guiding the flexible electrode array further comprises:
   delivering irrigation fluid via the cannulation channel, the irrigation fluids being dispensed through one or more irrigation openings in the elongated body.

32. The method of claim 25, wherein the flexible electrode array comprises multiple folded electrode strips defining the elongated body, and wherein the method further comprises:
   unfolding the multiple folded electrode strips defining the elongated body to deploy the unfolded electrode strips over the target area inside the body of the patient.

* * * * *

UNITED STATES PATENT AND TRADEMARK OFFICE
CERTIFICATE OF CORRECTION

PATENT NO. : 10,912,937 B2
APPLICATION NO. : 15/948625
DATED : February 9, 2021
INVENTOR(S) : James Kryzanski It is certified that error appears in the above-identified patent and that said Letters Patent is hereby corrected as shown below:

In the Claims

Column 14, Line 59, should read:
1. A device comprising:
an electrode comprising an elongated body having a length, a plurality of electrode contacts disposed on a substantially flat first side of the elongated body, and a cannulation channel defined along a longitudinal axis of the electrode, wherein the substantially flat first side of the elongated body extends along substantially the length of the elongated body; and
a guiding mechanism received within the cannulation channel, the guiding mechanism configured to guide the electrode for placement tangential to tissue in a subdural space of a patient.

2. The device of claim 1, wherein the cannulation channel is defined within the elongated body.

3. The device of claim 1, further comprising a sleeve disposed on a second side of the elongated body of the electrode, wherein the cannulation channel is defined by the sleeve.

4. The device of claim 3, wherein the second side of the elongated body is opposite the first side.

5. The device of claim 1, wherein the elongated body comprises a chain of body sections, wherein at least some of the body sections include tapered ends along a longitudinal axis of each of the at least some of the body sections, and wherein each of the plurality of electrode contacts is disposed at a respective different one of the body sections.

6. The device of claim 1, wherein the elongated body comprises a leading tip with an average width larger than a maximum body width of a remainder of the elongated body.

7. The device of claim 1, wherein the cannulation channel terminates at a reinforced area of a leading tip of the elongated body such that the cannulation channel is configured to cause the elongated body to be pulled into place from the leading tip using the guiding mechanism.

Signed and Sealed this
Thirtieth Day of July, 2024

Katherine Kelly Vidal
*Director of the United States Patent and Trademark Office*

8. The device of claim 1, wherein the cannulation channel is configured to receive irrigation fluids dispensed through a perforated end located near a leading tip of the elongated body.

9. The device of claim 8, further comprising an adapter fitted at an operator-end of the guiding mechanism, the adapter configured to at least direct the irrigation fluids from a fluid source for delivery via the cannulation channel.

10. The device of claim 9, wherein the adapter comprises a luer-lock.

11. The device of claim 1, wherein the guiding mechanism comprises a guidewire defining an internal channel between the guidewire and internal walls defining the cannulation channel, the internal channel configured to receive irrigation fluids dispensed through a perforated end located near a leading tip of the elongated body.

12. The device of claim 1, wherein the electrode further includes a radiopaque identifier element disposed proximate a leading tip of the elongated body.

13. The device of claim 1, wherein the elongated body comprises an elongated silicon-based elastomer body.

14. The device of claim 1, wherein each of the plurality of electrode contacts comprises one or more of: a stainless-steel contact, or a platinum contact.

15. The device of claim 1, wherein the electrode comprises multiple folded electrode strips defining the elongated body, the multiple folded electrode strip configured to be unfolded for deployment over the target area inside the body of the patient.

16. The device of claim 1, wherein the tissue in the subdural space is brain tissue of the patient.

17. An electrode comprising:
an elongated body having a length and a substantially flat first side of the elongated body, the substantially flat first side of the elongated body extending along substantially the length of the elongated body;
a plurality of electrode contacts disposed on the substantially flat first side of the elongated body; and
a cannulation channel defined along a longitudinal axis of the elongated body, the cannulation channel configured to receive a guiding mechanism to guide the electrode for placement tangential to tissue in a subdural space of a patient.

18. The electrode of claim 17, wherein the cannulation channel is defined within one of: the elongated body, or a sleeve disposed on a second side of the elongated body.

19. The electrode of claim 17, wherein the elongated body comprises a chain of body sections, wherein at least some of the body sections include tapered ends along a longitudinal axis of each of the at least some of the body sections, and wherein each of the plurality of electrode contacts is disposed at a respective different one of the body sections.

20. The electrode of claim 17, wherein the elongated body comprises a leading tip with an average width larger than a maximum body width of a remainder of the elongated body.

21. The electrode of claim 17, further comprising:
multiple folded electrode strips defining the elongated body, the multiple folded electrode strips configured to be unfolded for deployment over the target area inside the body of the patient.

22. A method comprising:
forming a hole to access target tissue in a subdural space of a patient;
coupling a guiding mechanism to an electrode comprising an elongated body having a length and a plurality of electrode contacts disposed on a substantially flat first side of the elongated body, the substantially flat first side of the elongated body extending along substantially the length of the elongated body; and
guiding the electrode, using the guiding mechanism, through the hole for placement tangential to the tissue in the subdural space of the patient.

23. The method of claim 22, wherein coupling the guiding mechanism to the electrode comprises:
inserting the guiding mechanism through a cannulation channel defined along a longitudinal axis of the elongated body of the electrode.

24. The method of claim 23, wherein inserting the guiding mechanism through the cannulation channel comprises one of:
inserting the guiding mechanism to the cannulation channel defined within the elongated body, or inserting the guiding mechanism to the cannulation channel defined in a sleeve disposed on a second side of the elongated body.

25. The method of claim 22, further comprising:
subsequent to placement of the electrode, repeating the coupling and guiding for one or more other electrodes for placement of the one or more other electrode at respective locations.

26. The method of claim 22, wherein the elongated body comprises a chain of body sections, wherein at least some of the body sections include tapered ends along a longitudinal axis of each of the at least some of the body sections, and wherein each of the plurality of electrode contacts is disposed at a respective different one of the body sections.

27. The method of claim 22, wherein the elongated body comprises a leading tip with an average width larger than a maximum body width of a remainder of the elongated body.

28. The method of claim 22, wherein guiding the electrode further comprises:
delivering irrigation fluid via the cannulation channel, the irrigation fluids being dispensed through one or more irrigation openings in the elongated body.

29. The method of claim 22, wherein the electrode comprises multiple folded electrode strips defining the elongated body, and wherein the method further comprises:
unfolding the multiple folded electrode strips defining the elongated body to deploy the unfolded electrode strips over the target area inside the body of the patient.

30. The device of claim 1, wherein the cannulation channel is further configured to, during progression of the electrode to the tissue in the subdural space, deliver irrigation fluid via an irrigation fluid passage defined through one or more of:

a space defined between a body of the guiding mechanism received within the cannulation channel and interior walls of the cannulation channel, or an interior channel defined within the body of the guiding mechanism received within the cannulation channel.